(12) United States Patent
Eipert et al.

(10) Patent No.: US 8,101,756 B2
(45) Date of Patent: Jan. 24, 2012

(54) PROCESS FOR THE PREPARATION OF QUATERNARY N-ALKYL MORPHIN OR MORPHINAN ALKALOID DERIVATIVES

(75) Inventors: Martin Eipert, Strengelbach (CH); Erik Heinz Lauterbach, Suhr (CH); Sabrina Heller, Oftringen (CH); Thomas Dinkel, Stengelbach (CH); Stephanie Hake, Rothrist (CH)

(73) Assignee: Siegfried Ltd., Zofingen (CH)

( * ) Notice: Subject to any disclaimer, the term of this patent is extended or adjusted under 35 U.S.C. 154(b) by 841 days.

(21) Appl. No.: 12/218,988

(22) Filed: Jul. 18, 2008

(65) Prior Publication Data
US 2009/0054651 A1    Feb. 26, 2009

(30) Foreign Application Priority Data
Jul. 19, 2007   (EP) .................................. 07112737

(51) Int. Cl.
*C07D 489/02*    (2006.01)
*C07D 489/08*    (2006.01)

(52) U.S. Cl. ................................ 546/45; 546/44; 546/46
(58) Field of Classification Search .................... 546/45, 546/44, 46
See application file for complete search history.

(56) References Cited

U.S. PATENT DOCUMENTS
4,176,186 A    11/1979   Goldberg et al.

FOREIGN PATENT DOCUMENTS
WO   WO2004/043964   5/2004

OTHER PUBLICATIONS

Extended European Search Report corresponding to European Patent Application No. 07112737.7 dated Feb. 28, 2008.

*Primary Examiner* — Charanjit Aulakh
(74) *Attorney, Agent, or Firm* — Jenkins, Wilson, Taylor & Hunt, P.A.

(57) ABSTRACT

The present invention relates to a process for the preparation of quaternary N-alkyl morphin or morphinan alkaloid derivatives. This is achieved by using a nucleophilic nitrogen, phosphor or sulfur containing base in the reaction mixture.

27 Claims, 5 Drawing Sheets

PROCESS FOR THE PREPARATION OF QUATERNARY N-ALKYL MORPHIN OR MORPHINAN ALKALOID DERIVATIVES

CROSS REFERENCE TO RELATED APPLICATIONS

This application claims the benefit of European patent application No. 07112737.7, filed Jul. 19, 2007, the entire disclosure of which is herein incorporated by reference.

FIELD OF THE INVENTION

The present invention relates to a process for the preparation of quaternary N-alkyl morphin or morphinan alkaloid derivatives.

BACKGROUND OF THE INVENTION

N-methyl quaternary derivatives of morphinan alkaloid such as naltrexone ((5α)-17-(cyclopropylmethyl)-4,5-epoxy-3,14-dihydroxymorphinan-6-one, sometimes referred to as N-cyclopropylmethyl-noroxymorphone) and naloxone (5α)-4,5-epoxy-3,14-dihydroxy-17-(2-propenyl)morphinan-6-one, sometimes referred to as N-allyl-noroxymorphone) have useful pharmacological properties as potent antagonists of the μ receptor. They bind to peripheral receptors primarily located in the gastrointestinal tract, act as antagonists and effectively mitigate some of the undesirable side effects of opiate therapy such as constipation and nausea. Because of their ionic charge, however, they do not traverse the blood brain barrier into the central nervous system; hence, the central activity of opiates responsible for pain relief is not blocked in the presence of these quaternary derivatives.

In U.S. Pat. No. 4,176,186, Goldberg et al. generally describe the preparation of quaternary derivatives of certain morphinan alkaloid by quaternizing a tertiary N-substituted morphinan alkaloid with a methylating agent such as methyl bromide, methyl iodide or dimethylsulfate. Goldberg et al. disclose that the methylating agent itself may be used as the solvent or, alternatively, another solvent medium such as methanol, ethanol, or other alcohols, methylene chloride, chloroform, tetrahydrofuran, dioxane, dimethylformamide, dimethylsulfoxide, acetonitrile, nitromethane or hexamethylphosphoric triamide may be used.

In WO 2004/043964 A2, Cantrell et al. disclose a process for the preparation and/or recovery of quaternary morphinan alkaloids. This process comprises contacting a tertiary N-substituted morphinan alkaloid with an alkyl halide in an anhydrous solvent system, wherein the solvent system comprises an aprotic dipolar solvent with the aprotic dipolar solvent constituting at least 25 wt % of the solvent system. Cantrell et al. further describe the recovery of the 3-hydroxy morphinan alkaloid by converting the alkaloid to a salt using a strong base. Examples of these strong bases comprise sodium methoxide, NaOH and KOH in methanol/water. However, the process of Cantrell et al. turned out to result in morphinan alkaloids containing considerable amounts of the alkylating agent used in the process.

SUMMARY OF THE INVENTION

Thus, it is an object of the present invention to provide a process for the preparation of quaternary N-alkyl morphin or morphinan alkaloid derivatives at a high purity and in high yield. A further object of the present invention is to provide a process for the preparation of quaternary N-alkyl morphin or morphinan alkaloid derivatives containing little or no alkylating agent in the final product. A still further object of the present invention is to provide a process for the preparation of morphin or morphinan alkaloid derivatives which process allows for the recovery of unreacted starting materials.

These objects are achieved by a process according to independent claim 1.

DETAILED DESCRIPTION OF THE INVENTION

The present invention refers to a process for the preparation of a quaternary N-alkyl morphin or morphinan alkaloid derivative of general formula (I) a or b:

formula (I) a formula (I) b wherein
A is —C(O)—, —C(S)—, —C(=CH$_2$)— or —CHA$_1$-,
A$_1$ is hydroxy, alkoxy, or acyloxy,
R$_1$ is hydrocarbyl or substituted hydrocarbyl,
R$_2$ is hydrocarbyl or substituted hydrocarbyl,
X$^-$ is an anion,
Y is hydrogen, hydroxy, alkoxy, or acyloxy,
starting from the tertiary N-alkyl morphin or morphinan alkaloid of general formula (II) a or (II) b formula (II) a formula (II) b wherein Z is hydroxy, alkoxy, or acyloxy,
via the intermediate zwitterion of formula (III) a or (III) b comprising the steps of:
  a) adding an alkylating agent to the compound of formula (II) a or b in presence of an aprotic, dipolar solvent to obtain a reaction mixture;
  b) adding a nucleophilic nitrogen, phosphor or sulfur containing base to the reaction mixture to obtain the intermediate zwitterion of formula (III) a or b in suspended or dissolved form;
  c) adding a solvent comprising alcohol and/or water to the product mixture thereby precipitating the compound of formula (III) a or b;
  d) separating the precipitated compound of formula (III) a or b from the remaining mixture; and
  e) suspending the intermediate zwitterion (III) a or b in water and adding a compound of formula HX to produce the product of formula (I) a or b.

Surprisingly, the inventors of the present invention found that the use of a nucleophilic nitrogen, phosphor or sulfur containing base in the reaction mixture results in an intermediate zwitterion which can be separated from the reaction mixture as a precipitate. This is unexpected since one would assume that a zwitterionic molecule of formula (III) would be more or less soluble in a polar solvent like alcohol and/or water. However, it turned out that in contrast thereto, the compound of formula (III) precipitates by adding a solvent comprising alcohol and/or water, which is an essential effect of the present invention.

The nucleophilic base further acts as a scavenger for unreacted alkylating agent.

Usually, alkylating agent is added at a stoichiometric excess in order to drive the reaction towards the alkylation of the alkaloid derivative. However, unreacted alkylating agent precipitates together with the desired alkaloid derivative and will thus be part of the product as undesired contaminant. In order to obtain an alkaloid derivative at a very high purity, the excess of the alkylating agent has to be removed. So far, there is no method known that can provide the separation of a quaternary N-alkyl morphin or morphinan alkaloid derivative and reduce the amount of alkylating agent in the final product at the same time.

In a first step, a tertiary N-alkyl morphin or morphinan alkaloid derivative is alkylated by a known alkylating agent, usually in the presence of an aprotic dipolar solvent. With the addition of a nucleophilic nitrogen, phosphor or sulfur containing base in a second step, the alkylated quaternary morphin or morphinan alkaloid derivative can be converted into its zwitterion by deprotonating the Z-group, in case Z is hydroxy, or by deprotecting Z, in case Z is alkoxy or acyloxy. In any case, a hydroxy group will result in the final product of formula (I). Further, the nucleophilic base reacts with excessive alkylating agent. The nucleophilic base is alkylated by the alkylating agent thus consuming the excess of alkylating agent.

In a further step, an alcohol and/or water is added to the reaction mixture causing the quaternary N-alkyl morphin or morphinan alkaloid derivative to precipitate from the reaction mixture. The precipitated compound can then easily be separated and finally converted into a compound of formula (I) a or (I) b by adding an acid of the general formula HX.

As outlined above, Z is hydroxy, alkoxy, or acyloxy. Preferably, Z is hydroxy or alkoxy. Most preferably, Z is hydroxy or methoxy. In general, Z may be selected from —$OCH_3$, —OAc—, OTHP, —$OSiR_3$ (wherein each R is independently hydrocarbyl, preferably lower alkyl), —OBn, —OBz, —OBs, —OTs, or —OMs.

Similarly, Y is selected from hydrogen, hydroxyl, alkoxy, or acyloxy. Preferably, Y is hydrogen or hydroxy. For the definitions of Y, all definitions for Z as given above equally apply.

The anion X may be any anion that can form a salt with compounds of formula (I) a or (I) b. Preferably, $X^-$ is a halide, such as iodide, chloride, or bromide. Further, $X^-$ may be selected from nitrate, sulfate, or phosphate. Further anions which can be used are borate, aluminate, silicate. Most preferably, $X^-$ is bromide.

It is noted that $X^-$ is not necessarily representing a whole molecule, but may also be a charge equivalent and represents always one negative charge only. For example, $X^-$ might be bromide (one negative charge; in this case $X^-$ is the whole molecule/atom), or in the case of, for example, sulphate, $(SO_4)^{2-}$, $X^-$ is one charge equivalent thereof only.

$R_1$ and/or $R_2$ are independently selected from hydrocarbyl or substituted hydrocarbyl. Preferably, $R_1$ and/or $R_2$ are selected from methyl, ethyl, propyl, allyl (—$CH_2CH=CH_2$), chloroallyl, cyclopropylmethyl, cyclobutylmethyl, or propargyl. $R_2$ may be further preferably selected from substituted or unsubstituted, saturated or unsaturated compounds of from 1 to 8 carbons.

In the above given definition of formulae (I)-(III), A is —C(O)—, —C(S)—, —C(=$CH_2$)— or —$CHA_1$-.

In a specific embodiment of the present invention, unreacted compounds of formula (II) a or (II) b which are still contained within the product mixture can be recycled.

The recycling can be achieved by reusing the reaction mixture adding further starting material.

Figure 1A:
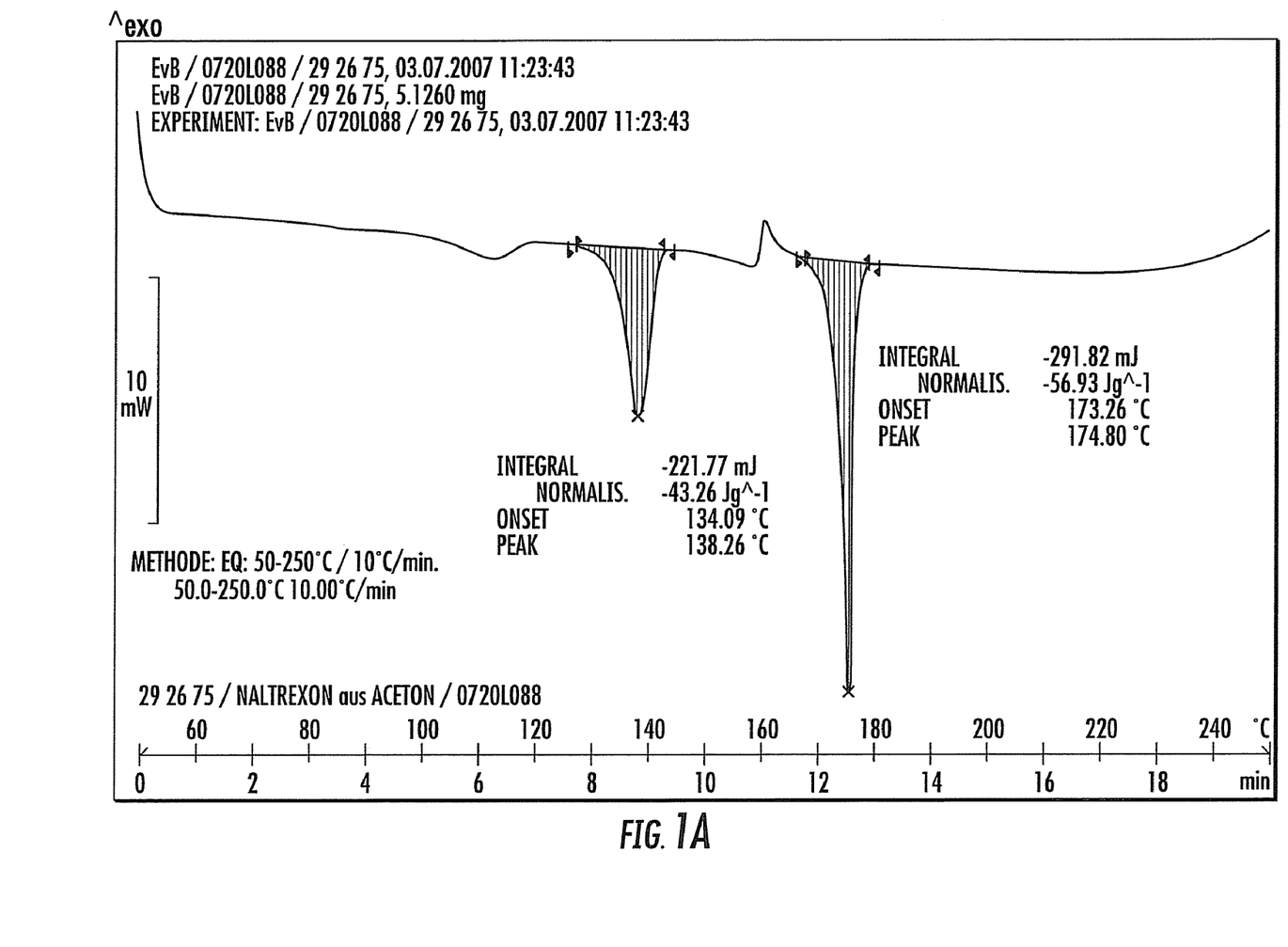
Figure 1B:
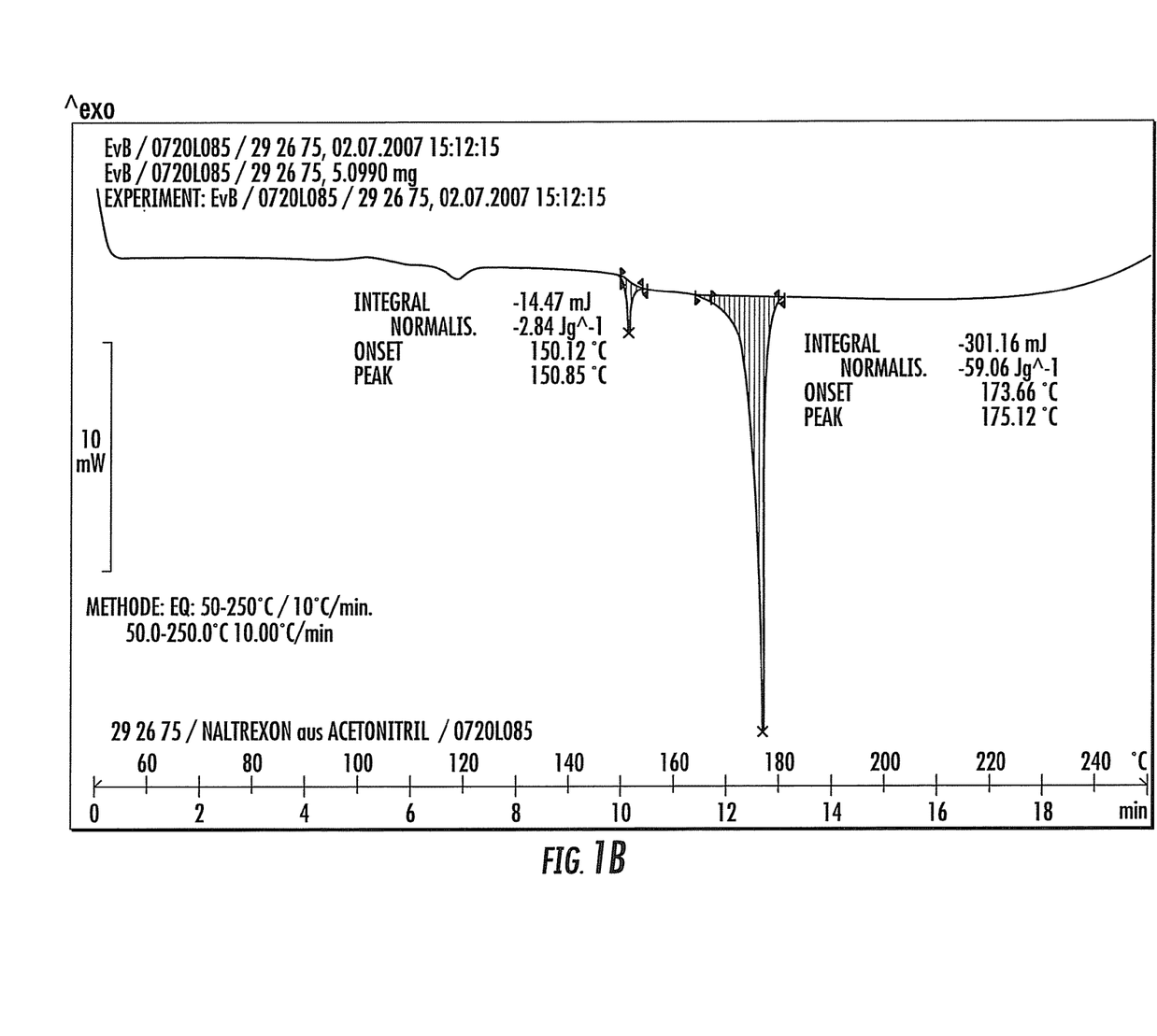
Figure 1C:
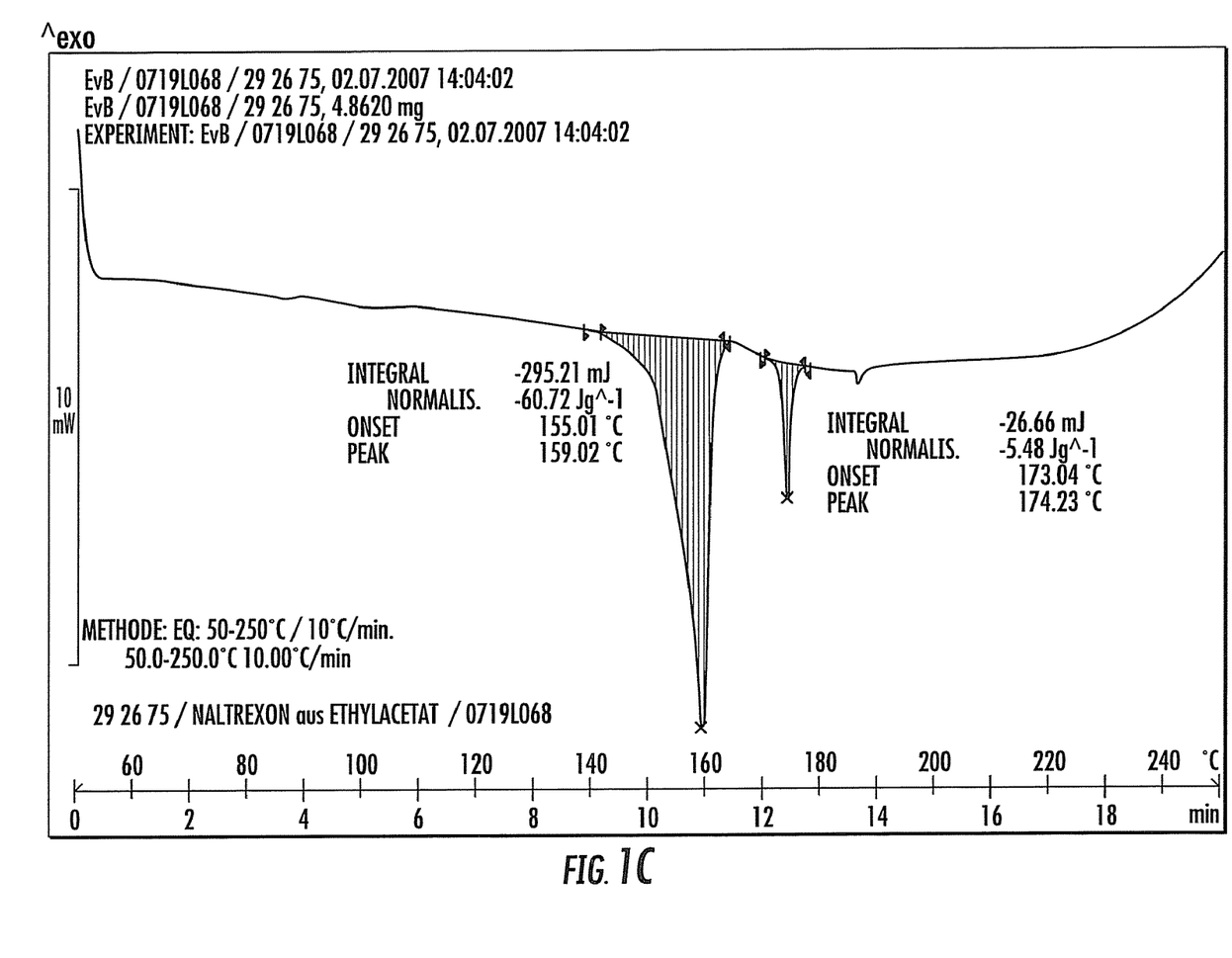
Figure 1D:
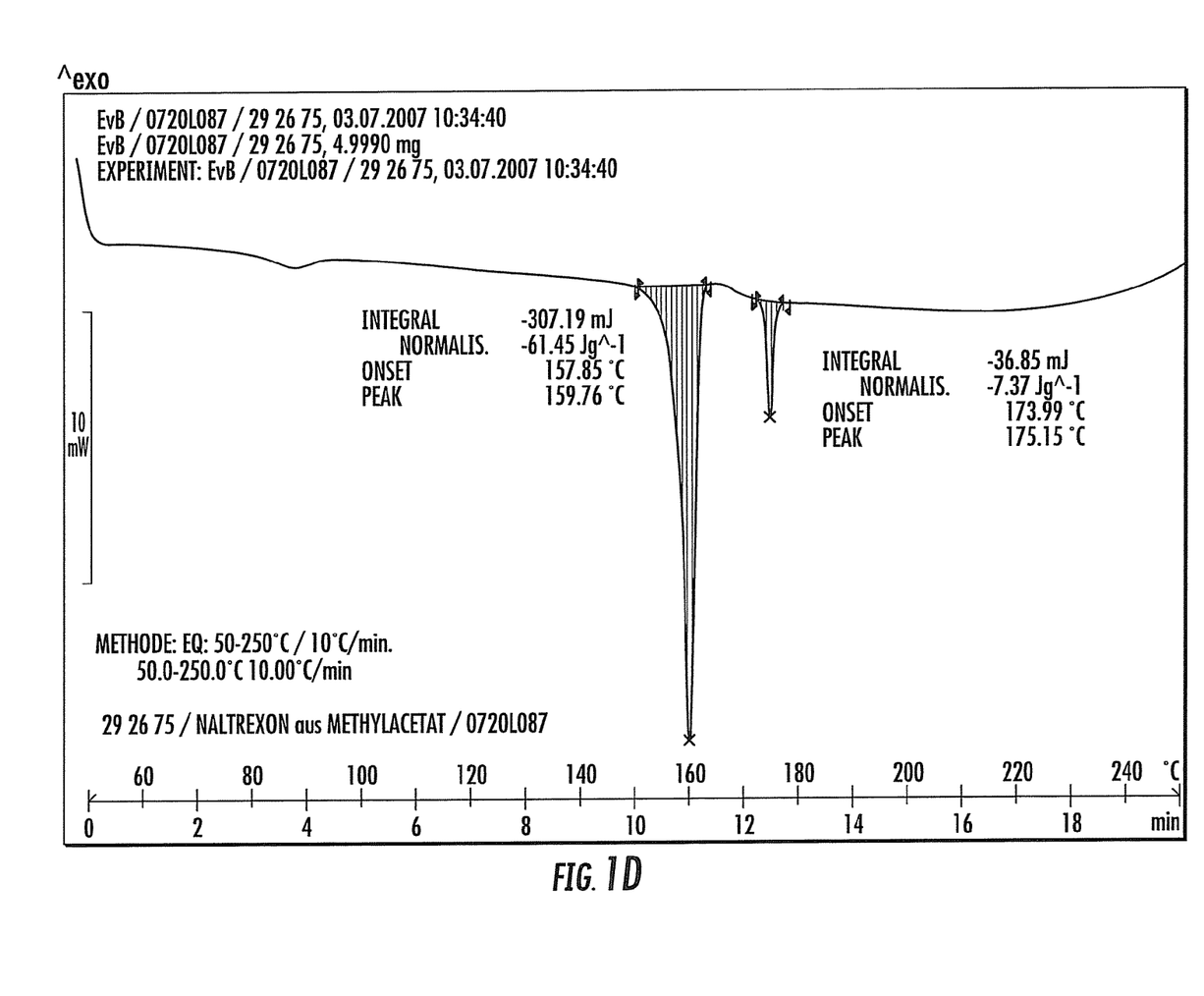
Figure 1E:
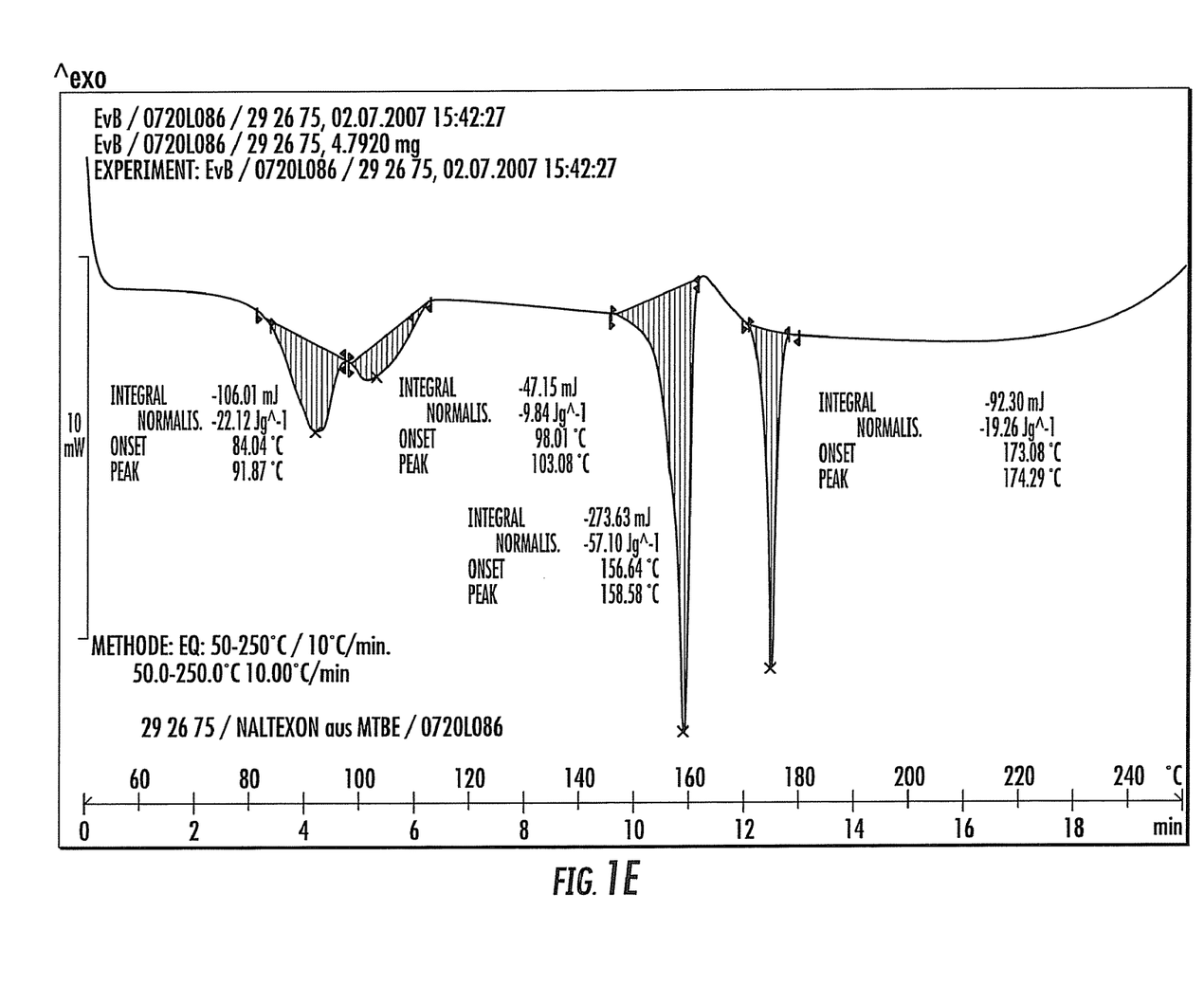

In a specifically preferred embodiment of the present invention, the following polymorph of the compound of formula (II) a or b is used as a starting material: the data are provided as two peaks of Differential Scanning Calorimetry (DSC)-measurements (for more detailed information, it is also referred to FIG. 1A-E) in different solvents:

TABLE 1

| solvent | Peak 1/° C. | Peak 2/° C. |
|---|---|---|
| acetone | 138.26 | 174.80 |
| acetonitrile | 150.85 | 175.12 |
| ethyl acetate | 159.02 | 174.23 |

TABLE 1-continued

| solvent | Peak 1/° C. | Peak 2/° C. |
|---|---|---|
| methyl acetate | 159.76 | 175.15 |
| MTBE (Methyl tert Butyl Ether) | 158.58 | 174.29 |

When N-alkylating the tertiary N-alkyl morphin or morphinan alkaloid, an alkylating agent of the general formula $R_2$-L is used, wherein $R_2$ is defined as above. Preferably, $R_2$ is selected from substituted or unsubstituted, saturated or unsaturated compounds of from 1 to 8 carbon atoms. L may be any leaving group, preferably a halide, like chloride, bromide or iodide, or an alkyl sulfate. More preferably, $R_2$ is methyl, ethyl, propyl, allyl, cyclopropyl, or benzyl. More preferably, L is chloride, iodide, bromide or methyl sulfate. In a specifically preferred embodiment, the alkylating agent is methyl bromide, preferably as water containing solution, preferably at a concentration of about 40-50 wt % MeBr, and most preferred at a concentration of 48 wt % MeBr. The solution may contain up to 2.5% by weight of water. The reminder comprises aprotic solvent.

When carrying out the alkylation of the alkaloid derivative, the starting material of formula (II) a or b is dissolved or suspended in an aprotic polar or dipolar solvent. Preferably, the aprotic solvent is selected from, but not restricted to, methanol, ethanol, acetone, methylene chloride, chloroform, tetrahydrofuran, dioxane, dimethylformamide, 1,3-dimethyl-2-imidazolidinone, dimethylsulfoxide, acetonitrile, nitromethane, dimethyl acetamide or hexamethylphosphoric triamide. As mentioned above, the reaction mixture of step a) may be in the form of a solution or suspension. The starting material may be completely or partly dissolved within the aprotic dipolar solvent.

The concentration of the compound of formula (II) a or b in the aprotic solvent may range from about 20-50 wt %, preferably from 30-40 wt %. For example, a preferred concentration is that of the compound of formula (II) in DMF of about 36 wt %. The concentration might be slightly lower if calculated on the basis of the content of the compound of formula (II) in a mixture of the aprotic solvent and the alkylating agent. Then, the ratio is approximately of from 20-30 wt %, for example about 27.5 wt % of formula (II) in a mixture of DMF and methyl bromide.

The alkylating agent usually is added at a ratio of starting material (formula (II)):alkylating agent of from 1:2 to 1:6, preferably about 1:3. As an example, the ratio from compound of formula (II) to methyl bromide might be about 1:3.2.

In a second step b), a nucleophilic nitrogen, phosphor or sulfur containing base is added to the reaction mixture. Preferably, the nucleophilic base is added at a molar ratio of alkylating agent nucleophilic base in the range of 1:0.3 to 1:6, preferably at a ratio of 1:2 to 1:4. The nucleophilic base may be selected from primary, secondary or tertiary amines, thiolates, primary, secondary or tertiary phosphines or phosphazanes. A person skilled in the art can without undue burden select any nucleophilic base that is capable of reacting with an alkylating agent. Most preferably, the nucleophilic base is diethylamine.

The preparation of the zwitterion of formula (III) a or b in step b) is preferably performed at temperatures between 10° C. and 100° C., more preferably at a temperature of 25-50° C., and most preferably at about 35° C.

In a further step c) the compound of formula (III) a or b is precipitated from the reaction mixture. This precipitation is achieved by the addition of alcohol and/or water. Preferably, the alcohol is selected from water miscible alcohols of from 1 to 4 carbon atoms. Most preferably, the alcohol is selected from methanol, ethanol, isopropanol, tert-butanol, or mixtures thereof. Preferably, a mixture of alcohol and water of about 1:1 is suitable. For example, water and methanol are mixed 1:1 (parts per weight). However, also other mixtures may be used, for example water alcohol of from 1:2 to 2:1.

The ratio of the above solvent (alcohol and/or water) to the reaction mixture (aprotic solvent+alkylating agent+compound of formula (III)) preferably is set as about 1:1, for example 0, 95:1. However, also other ratios might be selected as appropriate.

The ratio of the above solvent (alcohol and/or water) to the overall reaction mixture (aprotic solvent+alkylating agent+compound of formula (III)+base) is preferably about 1:1.5, for example about 1:1.66.

When adding the alcohol and/or water to the reaction mixture, the compound of formula (III) a or b precipitates as a zwitterion. This precipitation can be promoted by cooling the product mixture to a temperature of between 15° C. and 20° C., preferably 16-17° C.

Optionally, unreacted starting material of formula (II) a or b may be separated from the reaction mixture. This separation may be achieved by precipitating or extracting the unreacted compounds with a suitable solvent. More preferably, the solvent used for extraction may be selected from acetic ester, 2-butanone, 4-methyl-2-pentanone, tert-butyl-methylether, 3-methyl-2-butanone, dioxane, dichloromethane or tetrahydrofuran.

When performing the above given process according to the invention, the yield of the compound of formula (I) a or b is from 60 to 80 wt %, based on the amount of compound of formula (II) a or b used as starting material.

As used herein, "Ac" means acetyl, "Bn" means benzyl, "Bs" means bresyl, "Bz" means benzoyl, "Ms" means mesyl, "THP" means tetrahydropyranyl, and "Ts" means tosyl.

The term "anhydrous solvent" as used herein refers to solvents containing less than 0.5% by weight water, preferably maintained and handled under nitrogen gas during a reaction.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties.

These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20, preferably 1 to 10, most preferably 1 to 8 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, tertiary amino, amido, nitro, cyano, ketals, acetals, esters and ethers.

Unless otherwise indicated, the alkyl groups described herein are preferably lower alkyl containing from one to eight carbon atoms in the principal chain. They may be straight or branched chain or cyclic and include methyl, ethyl, propyl, isopropyl, allyl, benzyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "acyl", as used herein alone or as part of another group, denotes the moiety formed by removal of the hydroxyl group from the group —COOH of an organic carboxylic acid, e.g. RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy", as used herein alone or as part of another group, denotes an acyl group as described above bonded through an oxygen linkage (—O—), e.g. RC(O)O— wherein R is as defined in connection with the term "acyl".

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "halide" refers to fluoride, chloride, bromide, or iodide ions.

The present invention now is described in more detail by the accompanying figures and the examples.

DESCRIPTION OF THE FIGURES

The figures are showing the peaks received through DSC-data (Differential Scanning Calorimetry) of a preferred polymorph of the present invention (see also Table 1). The following solvents have been used in the different measurements:

FIG. 1 A: acetone
FIG. 1 B: acetonitrile
FIG. 1 C: ethyl acetate
FIG. 1 D: methyl acetate
FIG. 1 E: MTBE

EXAMPLES

Working Example 1

In a 500 ml round-bottom flask, 62.0 g dry DMF are introduced and cooled to a inner temperature (IT) of 0° C. under slow stirring. 30.0 g methyl bromide are condensed into at an external temperature of –40° C. and are allowed to drop in the cold DMF having a internal temperature of 0° C.

The resulting colourless solution is transferred to a round-bottom flask of 250 ml. The weight is 92 g; therefore, a solution of approximately 32-33 wt.-% in DMF is present.

In a 500 ml three neck flask, 35.0 g naltrexon are introduced at an inner temperature of 10-35° C. It is noted that the most preferred starting material is the polymorphic form of naltrexon which can be obtained by crystallisation from ethyl acetate.

At an inner temperature of 10-35° C., 92.0 g of the 32-33 wt.-% methyl bromide solution in DMF are added rapidly (within a few seconds). In doing so, a temperature change does not occur in the mixture and the starting material initially remains nearly unsolved.

The apparatus is sealed and a short term, low increase in pressure can be seen, which quickly returns to the original pressure.

The white suspension at first is vigorously stirred for 10 to 20 minutes at an inner temperature of 15-30° C. and, thereafter, is gradually heated (approximately 1-1.5° C./min) up to an inner temperature of 54° C. (admissible range of 53-55° C.; preferably 54-55° C.; maximum external temperature=60° C.).

As soon as the desired inner temperature of 54° C. is being reached, the reaction mixture is moderately stirred at this temperature for at least 24 h.

Following this reaction time, a thick white suspension has occurred.

The batch is slowly cooled under stirring from an inner temperature (IT) of 54° C. to 2° C. (–2 to 4° C.). At an IT 2° C. (–2 to 4° C.), 72.0 g diethylamine are slowly added in dry form via a dropping funnel in order to remove an excess of methyl bromide. By doing so, a strong exothermic reaction is occurring which, however, is declining within 1-2 minutes. The addition of the base should be performed in the beginning of the addition under circumstances, which ensure that the inner temperature of the quenched reaction batch stays below 45° C. It is optimal to reach a short time $IT_{MAX}$ of 40 to 45° C. The reaction mixture is brought back to room temperature as soon as possible (external cooling with an external temperature of 5-15° C.).

The quenched product solution is stirred for approximately 30-45 minutes at an IT of 20-30° C., and is then further cooled to an IT of 17° C. (admissible range of from 15-20° C.).

In a separate vessel, 60.0 g water are mixed with 60.0 g methanol. 120.0 g of the methanol-water mixture are slowly dropped via a dropping funnel to the moderately stirred reaction solution of IT 17° C. (admissible range of from 15-30° C.) (duration of addition: approximately 30±10 minutes). The addition is slightly exothermic (short term increase in temperature of about 5-10° C. to about IT 30° C.; after addition of about ½ of the overall solvent mixture, the product precipitates immediately as a powdery, white and easy-to-stir suspension.

After the termination of the addition, the suspension is stirred for 1-10 hours at an IT of 17° C. and is filtered off after that time.

Methylnaltrexon-betain is washed on the filter once with 41.0 g drinking water (15-30° C.). The humid product is dried over night at an IT of 50° C. (45-55° C.) and 10-50 mbar vacuum in a drying oven.

Yield: 27.7-29.4 g (approximately 66-70 wt.-%) of white methylnaltrexon-betain-trihydrate.

Working Example 2

In a 500 ml round-bottom flask, a solution of 83.4 g methyl bromide in DMA (34.5% by weight) are introduced.

In a 500 ml three neck flask, 100.0 g naltrexon are introduced at an inner temperature of 10-35° C. 14.8 g N,N-dimethyl acetamide and 4.3 g deionized water are added.

At an inner temperature of 20-25° C., 241.7 g of the methyl bromide solution in DMAc are added. The apparatus is sealed and is vented into an inflatable balloon.

The white suspension at first is heated to an inner temperature of 55° C. As soon as the desired inner temperature of 55° C. is being reached, the reaction mixture is moderately stirred at this temperature for at least 24 h.

Following this reaction time, a thick beige suspension has occurred.

The batch is slowly cooled under stirring from an inner temperature (IT) of 54° C. to 0-5° C. 206.0 g diethylamine are slowly added in dry form via a dropping funnel in order to remove an excess of methyl bromide. By doing so, a strong exothermic reaction is occurring which, however, is declining within 1-2 minutes. The addition of the base should be performed in the beginning of the addition under circumstances, which ensure that the inner temperature of the quenched reaction batch stays below 40° C.

The beige suspension is stirred for approximately 30 minutes at an IT of 20-25° C. In a separate vessel, 171.0 g water are mixed with 171.0 g methanol. The methanol-water mixture is slowly dropped via a dropping funnel to the moderately stirred reaction solution, the inner temperature is kept below 30° C. The batch is cooled to an inner temperature of 10-15° C. and is stirred at this temperature for at least 1 h. The suspension is filtered off after that time.

Methylnaltrexon-betain is washed on the filter once with 117.0 g deionized water. The humid product (94.20 g methylnaltrexon-betain) is dried for at least 16 h at an IT of 45° C. and 30 mbar vacuum in a drying oven.

Yield: 79.00 g of white methylnaltrexon-betain-trihydrate.

What is claimed is:

1. A process for the preparation of a quaternary N-alkyl morphin or morphinan alkaloid derivative of general formula (I) a or b:

formula (I) a formula (I) b wherein

A is —C(O)—, —C(S)—, —C(=CH$_2$)—, or —CHA$_1$-,

A$_1$ is hydroxy, alkoxy, or acyloxy,

R$_1$ is hydrocarbyl or substituted hydrocarbyl,

R$_2$ is hydrocarbyl or substituted hydrocarbyl,

X$^-$ is an anion,

Y is hydrogen, hydroxy, alkoxy, acyloxy, —O-tetrahydropyranyl (—OTHP), —OSiR$_3$, wherein each R is independently hydrocarbyl, —O-benzyl (—OBn), —O-benzoyl (—OBz), —O-bresyl (—OBs), —O-tosyl (—OTs), or —O-mesyl (—OMs), starting from the tertiary N-alkyl morphin or morphinan alkaloid of general formula (II) a or (II) b formula (II) a formula (II) b wherein Z is hydroxy, alkoxy, acyloxy, —OTHP, —OSiR$_3$, wherein each R is independently hydrocarbyl, —OBn, —OBz, —OBs, —OTs, or —OMs, via the intermediate zwitterion of formula (III) a or (III) b formula (III) a formula (III) b comprising the steps of:

a) adding an alkylating agent to the compound of formula (II) a or b in presence of an aprotic, dipolar solvent to obtain a reaction mixture;

b) adding a nucleophilic nitrogen, phosphorus or sulfur containing base to the reaction mixture to obtain the intermediate zwitterion of formula (III) a or b in suspended or dissolved form;

c) adding a solvent comprising alcohol and/or water to the product mixture thereby precipitating the compound of formula (III) a or b;

d) separating the precipitated compound of formula (III) a or b from the remaining mixture; and e) suspending the intermediate zwitterion (III) a or b in water and adding a compound of formula HX to produce the product of formula (I) a or b.

2. The process of claim 1, which further comprises recycling of unreacted compound of formula (II) a or b contained in the product mixture into step a).

3. The process of claim 1 or 2, wherein a polymorph of the compound of formula (II) a or b is used as a starting material, characterised by DSC (Differential Scanning calorimetry) data having main peaks in acetone at 138.26° C. and 174.80° C.; in acetonitrile at 150.85° C. and 175.12° C.; in ethyl acetate at 159.02° C. and 174.23° C.; in methyl acetate at 159.76° C. and 175.15° C.; and in methyl tert butyl ether (MTBE) at 158.58° C. and 174.29° C.

4. The method of claim 1, wherein the alkylating agent is represented by general formula $R_2$-L, wherein $R_2$ is defined as above; and L is a halide, or an alkylsulfate.

5. The method of claim 4, wherein $R_2$ is methyl, ethyl, propyl, allyl, cyclopropyl, or benzyl and/or L is chloride, iodide, bromide or methylsulfate.

6. The method of claim 1, wherein the alkylating agent is methyl bromide.

7. The method of claim 1, wherein the aprotic, dipolar solvent is selected from methanol, ethanol, acetone, methylene chloride, chloroform, tetrahydrofuran, dioxane, dimethylformamide, 1,3-dimethyl-2-imidazolidinone, dimethylsulfoxide, acetonitrile, nitromethane, dimethyl acetamide or hexamethylphosphoric triamide.

8. The method of claim 1, wherein the reaction mixture in step a) is in the form of a solution or suspension.

9. The method of claim 1, wherein the nucleophilic base is selected from primary, secondary or tertiary amines, thiolates, primary, secondary or tertiary phosphines or phosphazanes.

10. The method of claim 9, wherein the nucleophilic base is diethylamine.

11. The method of claim 1, wherein the alcohol used in step c) is selected from water miscible alkanols of from 1-4 carbons.

12. The method of claim 11, wherein the alkanol is selected from methanol, ethanol, isopropylic alcohol, tert-butanol, or mixtures thereof.

13. The method of claim 1, wherein the formation of intermediate zwitterion (III) a or b in step b) is performed at temperatures between 10° C. and 100° C.

14. The method of claim 1, wherein the precipitation in step c) is promoted by cooling the product mixture to a temperature of between 15° C. and 20° C.

15. The method of claim 1, wherein the molar ratio of alkylating agent to nucleophilic base is from 1:0.3 to 1:6.

16. The method of claim 15, wherein the molar ratio is from 1:2 to 1:4.

17. The method of claim 1, wherein the product obtained in step e) is purified, preferably by recrystallization.

18. The method of claim 2, wherein the recycling of unreacted compound of formula (II) a or b is performed by separating the compound from the reaction mixture by precipitation or extraction with a suitable solvent.

19. The method of claim 18, wherein the solvent used for extraction is selected from acetic ester, 2-butanone, 4-methyl-2-pentanone, tert-butyl-methylether, 3-methyl-2-butanone, dioxane, dichloromethane or tetrahydrofuran.

20. The method of claim 1, wherein the yield of the compound of formula (I) a or b is from 60 to 80 wt % based on the amount of compound of formula (II) a or b used as a starting material.

21. The method of claim 1, wherein the compound HX added in step e) is added as a water containing solution of about 50 wt %.

22. The method of claim 21, wherein the water containing solution is HBr 48 wt %.

23. The method of claim 1, wherein $R_2$ is saturated or unsaturated and from 1 to 8 carbons.

24. The method of claim 1, wherein the alkylating agent is water containing methyl bromide.

25. The method of claim 13, wherein the formation of intermediate zwitterion (III) a or b in step b) is performed at temperatures between 25 and 50° C.

26. The method of claim 25, wherein the formation of intermediate zwitterion (III) a or b in step b) is performed at about 35° C.

27. The method of claim 14, wherein the precipitation in step c) is promoted by cooling the product mixture to a temperature of between 16 and 17° C.

* * * * *